US007740424B2

(12) United States Patent
Pardini et al.

(10) Patent No.: US 7,740,424 B2
(45) Date of Patent: Jun. 22, 2010

(54) ARTICLE SEPARATION APPARATUS AND METHOD FOR UNIT OPERATIONS

(75) Inventors: Allan F. Pardini, Kennewick, WA (US); Kevin L. Gervais, Richland, WA (US); Royce A. Mathews, Kennewick, WA (US); Ronald L. Hockey, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 557 days.

(21) Appl. No.: 11/355,608

(22) Filed: Feb. 15, 2006

(65) Prior Publication Data

US 2007/0187296 A1 Aug. 16, 2007

(51) Int. Cl.
*B07B 9/00* (2006.01)
*B07B 7/00* (2006.01)
*B65G 47/36* (2006.01)
*G01M 19/00* (2006.01)
*G01N 33/00* (2006.01)

(52) U.S. Cl. ......................... 406/34; 73/865.8; 406/136

(58) Field of Classification Search .................. 406/34, 406/108, 113, 122–123, 136, 154–155, 164; 73/865.8–866; 209/20, 546, 567, 571, 138, 209/932

See application file for complete search history.

(56) References Cited

U.S. PATENT DOCUMENTS

| | | | | |
|---|---|---|---|---|
| 11,443 A * | 8/1854 | Shearman | 209/138 X |
| RE2,679 E * | 7/1867 | Brock | 209/138 |
| 893,479 A * | 7/1908 | Goldschmidt | 406/122 X |
| 1,271,834 A * | 7/1918 | Baum et al. | 209/138 X |
| 3,031,080 A * | 4/1962 | Lapple | 209/19 |
| 4,247,987 A * | 2/1981 | Coulaloglou et al. | 34/249 |
| 5,750,996 A * | 5/1998 | Drennen et al. | 250/341.2 |
| 6,152,448 A * | 11/2000 | Cudlipp | 273/144 R |
| 6,244,118 B1 * | 6/2001 | Andersson et al. | 73/863.52 |
| 2005/0029167 A1 * | 2/2005 | King et al. | 209/425 |

FOREIGN PATENT DOCUMENTS

| | | |
|---|---|---|
| WO | 9932872 A | 7/1999 |
| WO | 03028877 A | 4/2003 |

OTHER PUBLICATIONS

ISR/WO Search Rpt, Mar. 31, 2008, PCT.

Energy Products of Idaho (EPI), Fluidized Bed Combustion pp. 1-2.

Martin, et al., ORNL,Analytical Techniques for SiC Characterization: Literature Review and Project Status, pp. 1-64.

(Continued)

*Primary Examiner*—Thomas P Noland
(74) *Attorney, Agent, or Firm*—James D. Matheson

(57) ABSTRACT

An apparatus and method are disclosed for separating articles from a group of articles. The apparatus includes a container for containing one or more articles coupled to a suitable fluidizer for suspending articles within the container and transporting articles to an induction tube. A portal in the induction tube introduces articles singly into the induction tube. A vacuum pulls articles through the induction tube separating the articles from the group of articles in the container. The apparatus and method can be combined with one or more unit operations or modules, e.g., for inspecting articles, assessing quality of articles, or ascertaining material properties and/or parameters of articles, including layers thereof.

21 Claims, 11 Drawing Sheets

OTHER PUBLICATIONS

Hunn, et al., ORNL, Coated Particle Fuel Characterization Lab, presentation, Nov. 2003, 20 pages.
Nakagawa, Ames Laboratory, NERI Project Review, Jun. 2004, pp. 1-80.
Voice, et al., SiC in a Fluidized Bed of Microspheres, pp. 1-31.
DOE-HTGR-90257, Rev. 0, pp. 9-1 thur9-31.
Matsui, et. al., Key Eng Matl, vols. 125-126, 1997, pp. 249-282.
Ogawa, et al., Journal of Nuclear Materials, 98, 1981, pp. 18-26.
Sawa, et al., Nuclear Engineering and Design, 208, 2001, pp. 305-313.
Sawa, et al, Journal of Nuclear Science and Technology, vol. 38, No. 6, Jun. 2001, pp. 403-410.
Charollais, et al., 2nd International Topical Meeting, Sep. 22-24, 2004, Paper B04, pp. 1-11.
Kamsani, et al., Ministry of Develpment, The Use of Mgnetic Potentiometers in Steel Crack Detection , pp. 1-3, copyright 1998-1999.

* cited by examiner

ARTICLE SEPARATION APPARATUS AND METHOD FOR UNIT OPERATIONS

This invention was made with Government support under Contract DE-AC05-76RLO1830 awarded by the U.S. Department of Energy. The Government has certain rights in the invention.

FIELD OF THE INVENTION

The invention relates generally to an article separation apparatus and method for unit operations. The invention finds application in areas including, but not limited to, e.g., material handling, manufacturing, in-process control, quality assessment, inspection, and the like.

BACKGROUND OF THE INVENTION

Quality control (QC) systems and methods for inspecting small articles frequently employ destructive testing not suited to in-process and/or on-demand fabrication measurements and assessments. Destructive testing, for example, can be economically infeasible for assessing quality of batches involving substantial quantities of small (micron range) articles, e.g., nuclear fuel particles. Nor can such systems be expected to meet the demand anticipated in future high throughput production processing.

Accordingly, new material inspection systems and methods are needed to reduce the number of independent measurements needed to qualify articles in a batch and further address quality control and assessment issues and thereby meet production throughput requirements.

SUMMARY OF THE INVENTION

In one aspect, the invention is an apparatus for separating articles in a group of articles, comprising: a containing means for containing one or more articles defining a group of articles, the containing means comprising an inlet for introducing the one or more articles into the containing means and one or more outlets; a levitating means for levitating the one or more articles in the group of articles within the containing means whereby articles are introduced singly to the outlets; one or more conduits operatively coupled to the outlets for transporting the single articles away from the group of particles via differential pressure; and thereby separating the single articles from the group of articles in the containing means.

In another aspect, the invention is a method for separating articles in a group of articles, comprising the steps: providing a containing means for containing one or more articles defining a group of articles, the containing means comprising an inlet for introducing the one or more articles into the containing means and one or more outlets; a levitating means for levitating the one or more articles in the group of articles within the containing means whereby articles are introduced singly to the outlets; one or more conduits operatively coupled to the outlets for transporting the single articles away from the group of particles via differential pressure; and thereby separating the single articles from the group of articles in the containing means.

In one embodiment, conduits are selected from induction tube, vacuum tube, pick-up tube, or the like, or combinations thereof.

In another embodiment, a containing means is selected from hoppers, feeders, funnels, enclosures, containers, magnetic bottles, chambers, conduits, piping, or the like, or combinations thereof.

In another embodiment, conduits include a portal for introducing articles thereto, the conduits being positioned within a volume of the containing means traversed by the one or more articles levitated by the levitating means, whereby agitation of the articles proximate the portal within the volume minimizes clumping or aggregation of the articles thereat facilitating introduction of single articles thereto.

In another embodiment, a portal is located on an introduction surface of the conduit(s), the surface having a shape selected from flat or round.

In another embodiment, positioning of the conduits and/or portal includes an angle of rotation selected with respect to a virtual axis projected along the length of the conduits and/or the portal from about 0 degrees to about 90 degrees clockwise or counterclockwise relative to a direction of levitation produced by the levitating means.

In another embodiment, positioning of a portal involves a movement of the conduits within a volume of the containing means selected from horizontal, lateral, vertical, oblique, transverse, or the like, or combinations thereof.

In another embodiment, one or more unit operations or modules are coupled to the conduits for performing one or more operations on the one or more articles transported within the conduits.

In another embodiment, the one or more unit operations or modules are selected from inspection, coating, quality assessment, or combinations thereof.

In another embodiment, one or more operations or modules includes an inspection operation or module comprising a sensor selected from the group of inductive, capacitive, optical, acoustic, magnetic, infra-red, X-ray, tomographic, radiographic, coating, or combinations thereof.

In another embodiment, a sensor is an inductive sensor having an inductive coil.

In another embodiment, a coil of an inductive sensor is disposed within a portal of a conduit(s) coincident with or protruding from an introduction surface of the conduit(s) thereby minimizing dead volume for articles introduced to the conduit(s).

In another embodiment, a coil of a sensor is positioned at a displacement angle with respect to a virtual axis projected through the center of the coil selected in the range from about 0 degrees to about 90 degrees for operation of the same.

In another embodiment, a vertical plane of an inductive coil is positioned at an angle relative to the vertical plane of a levitating direction selected in the range from about 0 degrees to about 90 degrees for introducing articles to a conduit(s).

In another embodiment, one or more operations or modules include an inductive sensor for measuring a conductive property of articles.

In another embodiment, one or more operations or modules includes a coating operation or module.

In another embodiment, at least one operation or module is operable for measuring a physical property of an article(s) or a layer thereof.

In another embodiment, an inspection operation(s) or module(s) includes an inductive sensor for measuring a conductive property of articles.

In another embodiment, an inspection operation(s) or module(s) includes a capacitive sensor for measuring a non-conductive property of articles.

In another embodiment, an inspection operation(s) or module(s) is operable for measuring a physical property of articles or a layer thereof.

In another embodiment, a physical property measured for an article(s) is selected from size, presence of a material, absence of a material, thickness, shape, conductance, non-conductance, dielectric constant, variances in same, or combinations thereof.

In another embodiment, a physical property measured for a layer(s) of an article(s) is selected from thickness, anisotropy, uniformity, presence of a material, absence of a material, non-conductance, conductance, dielectric constant, variances in same, or combinations thereof.

In another embodiment, a physical property measured for an article(s) is a conductive property.

In another embodiment, a physical property measured for an article(s) is a non-conductive property.

In another embodiment, a physical property measured for an article(s) and/or a layer thereof is a defect selected from layer variations, concentricity variations, uniformity variations, spatial uniformity variations, cracks, flats, or combinations thereof.

In another embodiment, articles are of a size selected in the range from about 0.1 mm to about 5 mm, or from about 0.1 mm to about 3 mm, or from about 0.3 mm to about 1 mm.

In an embodiment, the apparatus and/or method is used in a pharmaceutical production system or process.

In an embodiment, the apparatus and/or method is used in a nuclear fuel production system or process.

BRIEF DESCRIPTION OF THE DRAWINGS

A more complete appreciation of the invention will be readily obtained by reference to the following description of the accompanying drawing in which like numerals in different figures represent the same structures or elements.

TERMS

Figure 1:
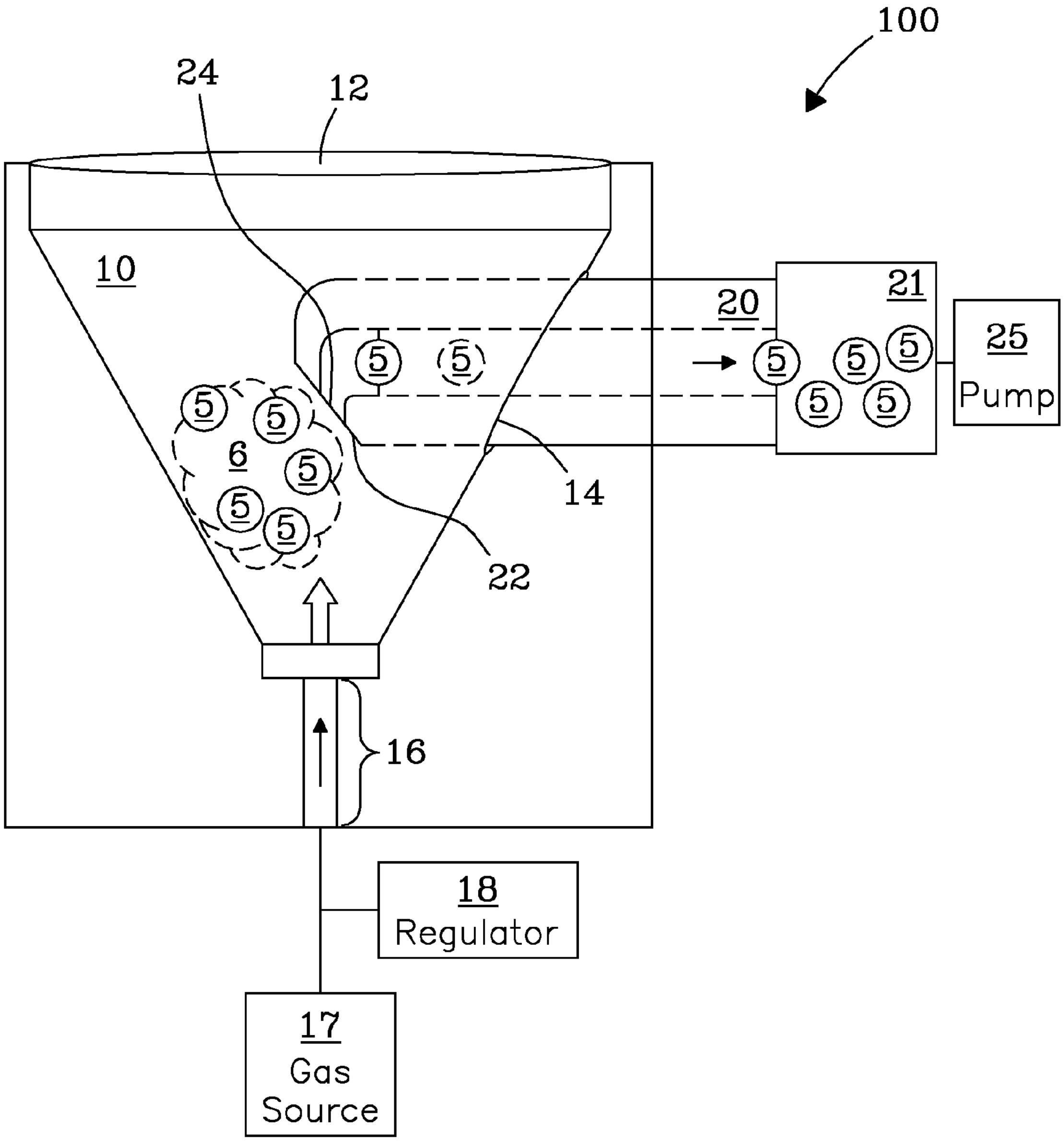
FIG. 1 illustrates an apparatus of a benchscale design for separating articles, according to an embodiment of the invention.

The term impedance (Z) as used herein has its customary and ordinary meaning as will be understood by those of skill in the art. Impedance (measured in Ohms) measures combined resistance (R) and reactance (X) to current flow due to presence of, e.g., inductive and/or capacitive elements. Inductive reactance is equal to [2*π*frequency (f)*inductance (L)]. Capacitive reactance is equal to [1/(2*π*frequency (f)*capacitance (C)].

The term fractional impedance as used herein refers to the difference in measured impedance values divided by a reference impedance, i.e., ($\Delta Z/Z$ or $Z_1-Z_0/Z_0$).

The term "inductive" as used herein refers to devices and/or systems inducing electromagnetic fields in conductive materials, e.g., for detecting flaws, determining thickness, inspecting, measuring conductivity, or the like therefrom.

The term "TRISO" is an abbreviation for "tristructural isotropic" used to describe a fully coated fuel particle tested in conjunction with the invention. TRISO particles tested include three isotropic (uniform property) layers: 1) an inner pyrolytic carbon layer, 2) a silicon carbide (SiC) layer, and 3) an outer pyrolytic carbon layer covering a buffer-coated fuel kernel of, e.g., $UO_2$, uranium oxycarbide, or (surrogate kernel) zirconium oxide ($ZrO_2$). The term "isotropic" means a layer is independent of the axis of testing. The term "pyrolytic carbon" (or pyrocarbon) (PyC) as used herein refers to one or more layers of a TRISO or surrogate TRISO fuel particle. Pyrolytic carbon belongs to the family of turbostratic carbons having a structure wherein the layers are disordered giving the pyrolytic carbon improved durability compared to graphite. Pyrolytic Carbon layers include, e.g., inner PyC (IPyC) and outer PyC (OPyC) layers.

The term "coating" as used herein refers to a covering comprising one or more layers of the same or different materials.

DETAILED DESCRIPTION OF THE INVENTION

The invention relates generally to an article separation apparatus and method for unit operations. The term "article" as used herein is an article of manufacture of a substantially small size. Articles include, but are not limited to, e.g., microspheres, nanospheres, macrospheres, pebbles, particles, tablets, or the like of any shape, including, but not limited to, e.g., spherical, ovoid, rectangular. The invention finds application in areas including, but not limited to, e.g., material handling, manufacturing, in-process measurement and control, quality assessment and control, inspection, and in conjunction with various unit operations or modules. For example, the invention provides article handling capabilities suited for inspection and/or quality-control (QC) assessment of manufactured items, e.g., in the pharmaceutical and nuclear industries. In one exemplary QC assessment described herein (Example 1), for example, detection of articles and/or particles with unacceptable coating and/or layer thicknesses are made that may provide for (i) in-line measurements, (ii) on-process measurements and/or (iii) advanced off-line non-destructive examination (NDE) measurements for addressing quality issues. The invention may further improve QC testing of other processes involved in manufacturing. No limitations are intended. The invention is expected to find applications in the nano/micro-material nuclear, pharmaceutical, chemical, and biotechnology (e.g., in the bioseed and/or biobead) industries wherein accurate, rapid, high volume and/or high-speed measurements for assorted articles are required. Additionally, the invention is applicable for in-process measurements whereby material properties and/or physical parameters of articles and article layers can be assessed, including, e.g., uniformity, thickness, and the like. No limitations are intended. The term "layer" as used herein refers to a single thickness of a homogeneous material or substance providing a specific function and/or property to an article. Layers may comprise one or more materials in combination thus exhibiting layer patterns. For an article constructed of three (3) layers, for example, layer patterns might include, e.g., A-A-A, A-B-A, A-A-B, A-B-C, B-A-B, B-A-C, or combinations thereof, where A, B, and C represent different materials of which layers of the article are composed. Materials associated with articles and layers thereof include, but are not limited to, e.g., conductive, non-conductive, dielectric, ceramic, polymer, inorganic, organic, powdered, glass, or combinations thereof, as will be understood by those of skill in the art. No limitations are intended. Conductive materials include, e.g., metals (e.g., copper, tin), semiconductive materials, pyrolytic carbons, or combinations thereof. Dielectric materials include, but are not limited to, e.g., metal oxides, ceramics, glasses, plastics, silicon carbide, or combinations thereof. Organic materials include, but are not limited to, e.g., seeds, beans, peas, or the like, or combinations thereof. No limitations are intended.

One or more unit operations or modules may be coupled or used in conjunction with the invention thereby providing, e.g., inspection of an article, coating of an article, or another end result associated with manufacturing. Unit operations or modules include, but are not limited to, e.g., inspection, coating, quality assessment, or like operations, or combinations thereof. For example, some operations or modules provide measurement of selected physical properties (e.g., conductive or non-conductive properties) of articles including layers thereof. Other operations or modules bring about an end result or condition, e.g., coating of an article in a manufacturing process. As will be understood by those of skill in the art, operations and/or modules may further include techniques, devices, sensors, and/or associated systems for measuring and/or collecting data. No limitations are intended.

In one illustrative example, techniques and devices suitable for use in conjunction with unit operations or modules include, but are not limited to, e.g., electromagnetic, inductive, capacitive, acoustic, ultrasonic, optical, infra-red, magnetic, tomographic, topographic, radiographic, X-ray, imaging, or combinations thereof. Acoustic techniques and devices include, but are not limited to, e.g., acoustic sensors, acoustic microscopy, transmission ultrasound, pressurized gas-coupled ultrasound, backscatter ultrasound, scattering and diffuse field ultrasound, Resonant Ultrasound Spectroscopy (RUS), ultrasonic resonance, or the like, or combinations thereof. Optical techniques and devices include, but are not limited to, e.g., optical sensors, photonic, fiber optic, interferometry, laser Doppler, visible light, invisible light, time-of-flight, or combinations thereof. Infra-red techniques and devices include, but are not limited to, e.g., infra-red sensors, near infra-red, far infra-red, temperature, reflective object, or combinations thereof. Magnetic resonance and imaging sensors include, but are not limited to, e.g., handheld, field-portable, microscale, density and/or flow imaging, RF, magnetic susceptibility, planar RF, functional, nanoliter volume, cellular mass spectrometry, multiplexed, wavelet transform, spectral estimation, real-time dynamic, neural network, neuronal ensembles, micropatterned, magnetic field, speed, proximity, thickness gauge, flaw, screener, classifier, separator, magnetic thin film, or the like, or combinations thereof. No limitations are intended. Thickness gauges, for example, are used to make precise dimensional measurements on a wide variety of coatings and materials including, but not limited to, e.g., steel, plastic, glass, rubber, ceramics, paint, electroplated layers, enamels, or combinations thereof. X-ray techniques and devices include, but are not limited to, e.g., linear, hybrid, monolithic, CCDs, transistor arrays, drift detectors, wireless, digital, or the like. Electromagnetic techniques and devices include, but are not limited to, e.g., passive, active, or the like. Tomographic techniques and devices include, but are not limited to, e.g., electrical resistance, electrical texture, electrical capacitance, electrical impedance, x-ray, gamma-ray, microwave, process, reflection, transmission, or the like, or combinations thereof. Listed techniques and devices can be utilized in a wide variety of ways as will be understood by those of skill in the art, including, but not limited to, e.g., process monitoring and control, automotive examination, chemical analysis, medical imaging, material property measurements, and the like, or combinations thereof. No limitations are intended by the disclosure. All unit operations, modules, technique and/or device configurations as will be implemented by those of skill in the art are within the scope of the instant disclosure and are encompassed hereby.

An apparatus for separating articles from a group of articles will now be described in reference to FIG. 1.

FIG. 1 illustrates an apparatus 100 of a benchscale design for separating single articles 5 (e.g., particles, tablets, or other manufactured articles) from a group of articles, according to an embodiment of the invention. Apparatus 100 includes a containing means 10 for containing one or more articles (e.g., in a group of articles) therein. Containing means 10 include, but are not limited to, e.g., hoppers, feeders, funnels, enclosures, containers, magnetic bottles, chambers, conduits, piping, or the like. Containing means 10 is configured with an inlet 12 for introducing articles 5 to containing means 10 and an outlet 14. In other embodiments, containing means 10 includes one or more outlets 14 providing multiple exit paths from containing means 10. In the instant embodiment, containing means 10 further includes a levitating means 16 for suspending and transporting articles 5 within containing means 10. The term "levitating" as used herein refers to any mechanism or process whereby articles are suspended and transported, including, but not limited to, e.g., bubbling, lifting, flowing, rotating, streaming, conveying, moving, or combinations thereof. Levitating means 16 include, but are not limited to, e.g., separators, aerators, fluidizers, channels and/or channeling devices, conduits, charging devices (e.g., antistatic chargers), projecting devices, pneumatic devices, propellers, and like systems, devices, and/or components. For example, articles may be suspended within a containing means using a fluidizer in conjunction with use of a fluid (e.g., a non-conducting fluid). No limitations are intended. In the instant embodiment, levitating means 16 is a channel delivering a stream of compressed gas (e.g., air) controlled via regulator 18 from, e.g., a compressed gas source 17 generating a plume 6 of suspended articles 5 having a suitable (e.g., vertical) direction of flow or levitation within containing means 10. Plume 6 further functions to remove dust or other contaminants present in the plume 6 of suspended articles 5 from containing means 10, e.g., in conjunction with a filter or screen (not shown). Conduit 20 (e.g., induction tube, vacuum tube, pickup tube, or the like) provides an exit path for transporting of articles 5 away from containing means 10 coupling to containing means 10 through outlet 14. In the instant embodiment, conduit 20 is an induction (vacuum) tube 20 that extends horizontally [(e.g., about 1.5 inches (3.81 cm)] into containing means 10. Conduit 20 connects to a pump 25 (e.g., a vacuum pump) or other means establishing a differential pressure or vacuum therein for pulling articles 5 through conduit 20 separating articles 5 introduced thereto from a group of articles within containing means 10. Conduit 20 further includes an introduction surface 22 with a portal 24 (opening) therein through which articles enter into conduit 20. Shape of introduction surface 22 is not limited. In the instant embodiment, for example, introduction surface 22 is flat, but is not limited thereto. In another embodiment, introduction surface 22 is round. Surface 22 is further fashioned at an angle of about 45 degrees relative to a virtual axis projected along the length of conduit 20, but is not limited. Portal 24 of introduction surface 22 is positioned in containing means 10 within the plume 6 of suspended articles 5 providing optimum transfer of articles 5 introduced thereto. Portal 24 is preferably of a size permitting only a single article 5 to enter conduit 20, but again is not limited. Portal 24 is further rotated clockwise or counterclockwise about a virtual axis projected along the length of conduit 20 to an angle in the range from about 0 degrees to about 90 degrees relative to the direction of levitation provided by levitating means 16 optimizing introduction of articles 5 through portal 24. At the selected angle, agitation of articles 5 proximate portal 24 in the plume 6 of suspended articles 5 minimizes clumping or aggregation of articles 5 introduced at portal 24. Positioning and orientation of conduit 20 and/or portal 24 within containing means 10 is not limited. For example, positioning is effected by moving conduit 20 horizontally, laterally, vertically, obliquely, transversely, or the like, or combinations thereof. Selection of a suitable location for outlet 14 further optimizes positioning of conduit 20 and/or portal 24.

A collection means 21 (e.g., collection tube, collection vessel, or the like) is optionally attached to conduit(s) 20 for collecting articles transported through conduit(s) 20. Containing means 10 and conduit(s) 20 are preferably composed of insulating materials including, but not limited to, e.g., non-conductive polymers, acrylics, glasses, rubbers, and the like. No limitations are intended. In one embodiment, containing means 10 and conduit 20 are machined of acrylic for viewing articles therein, but material is not limited thereto. Articles 5 can be collected from conduits 20 introduced to containing means 10 as will be understood by those of skill in the art. No limitations are intended.

FIG. **2*a* illustrates a top-down perspective view of containing means 10, showing positions for inlet 12, outlet 14, and levitating means 16, according to one embodiment of the invention. Containing means 10 is shown with articles 5** therein.

FIG. **2*b* presents a vertical cross-sectional view of containing means 10, according to one embodiment of the invention. Exemplary dimensions are shown in the figure, including those for outlet 14 and levitating means 16** therein.

FIG. **2*c* presents a cross-sectional view of conduit 20 of the article separation apparatus that transports single articles separated from the containing means, according to one embodiment of the invention. In the figure, conduit 20 includes introduction surface 22 (flat) with portal 24 located therein for introducing articles (described previously with reference to FIG. 1) to conduit 20**. The plane of the introduction surface is at an angle ($\theta_1$) of from about 40 degrees to about 50 degrees with respect to the axis defined along the length of the conduit, 45 degrees being preferable.

Figure 2A:
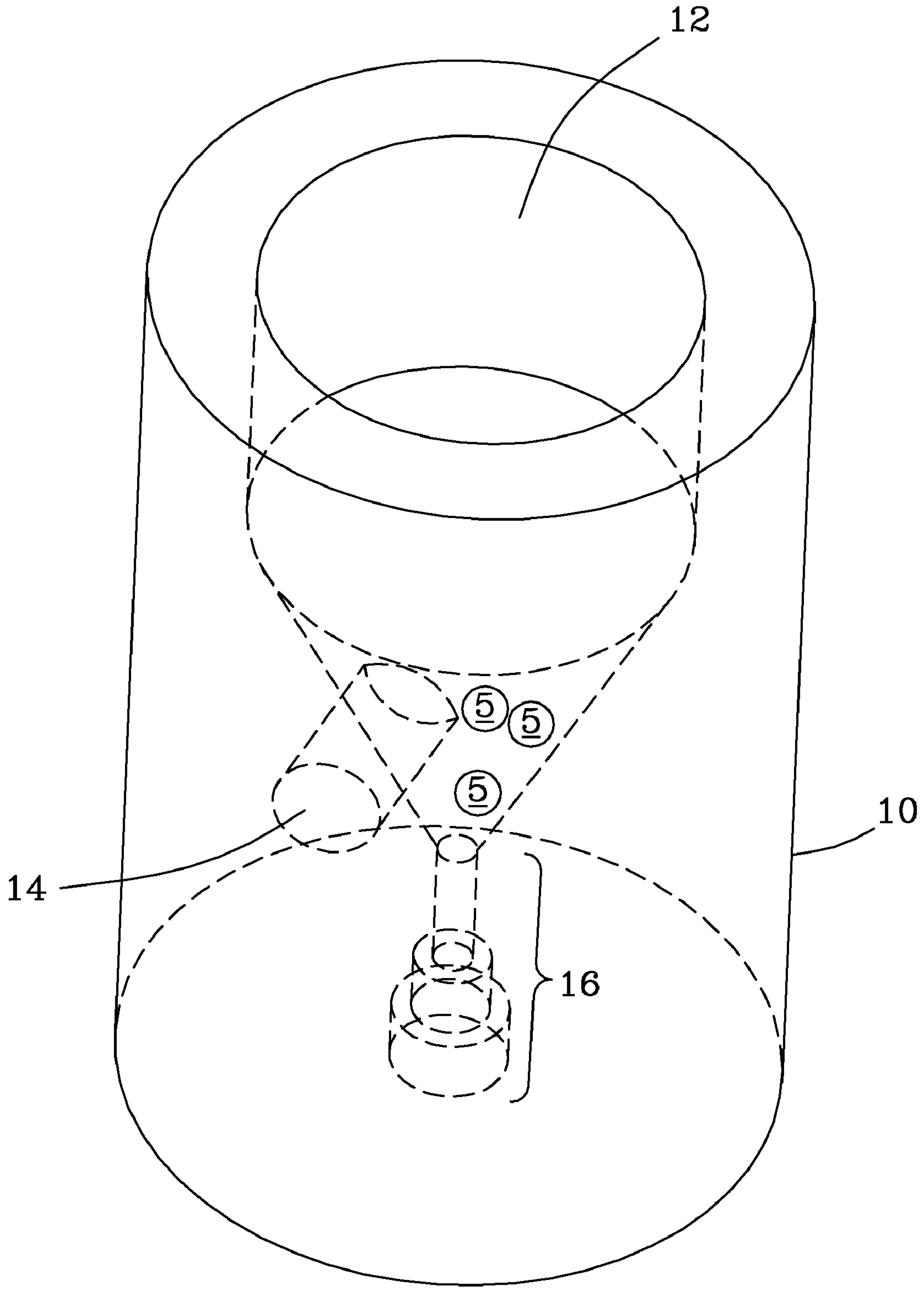
FIG. 2*a* presents a top-down whole view of a containing means, according to an embodiment of the invention.
Figure 2B:
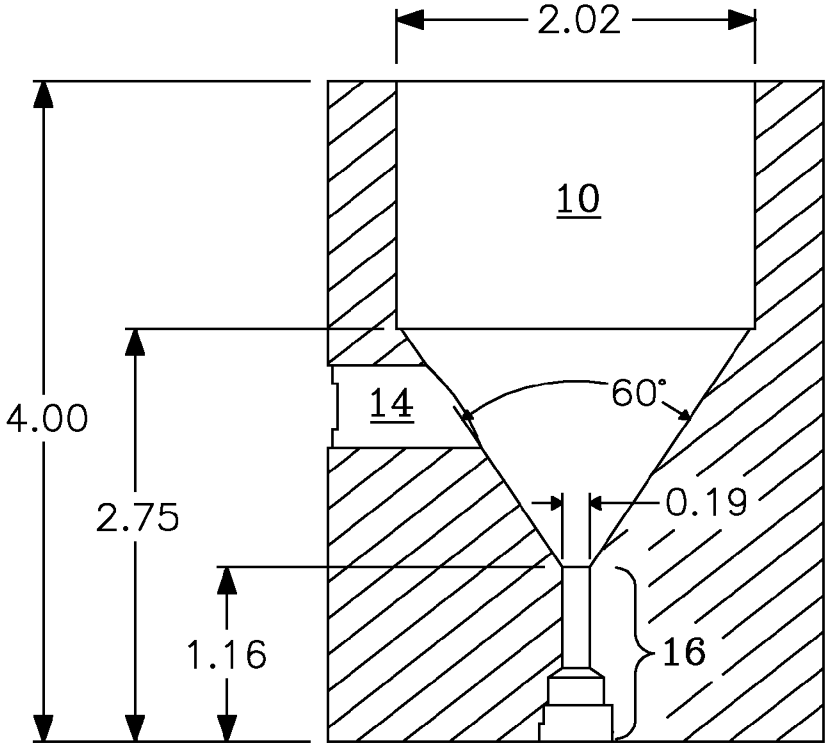
FIG. 2*b* presents a vertical cross-sectional view of a containing means, according to an embodiment of the invention.
Figure 2C:
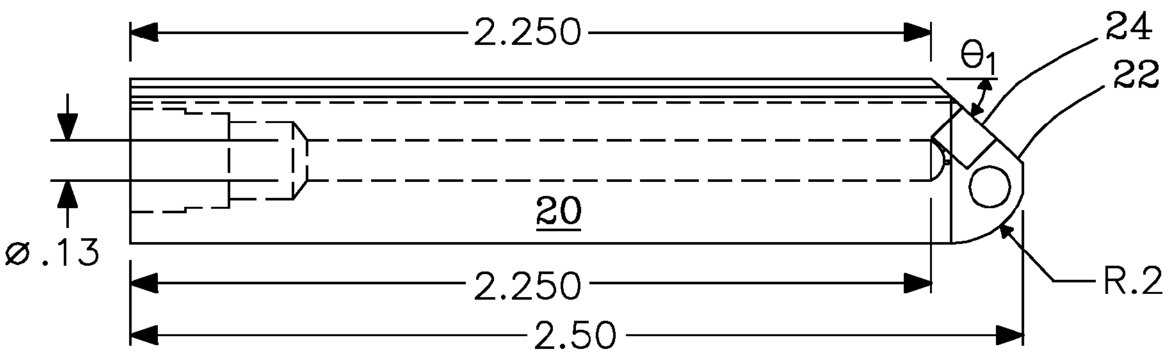
FIG. 2*c* presents a cross-sectional view of a conduit that couples to containing means for transporting articles from containing means, according to an embodiment of the invention.
Figure 2D:
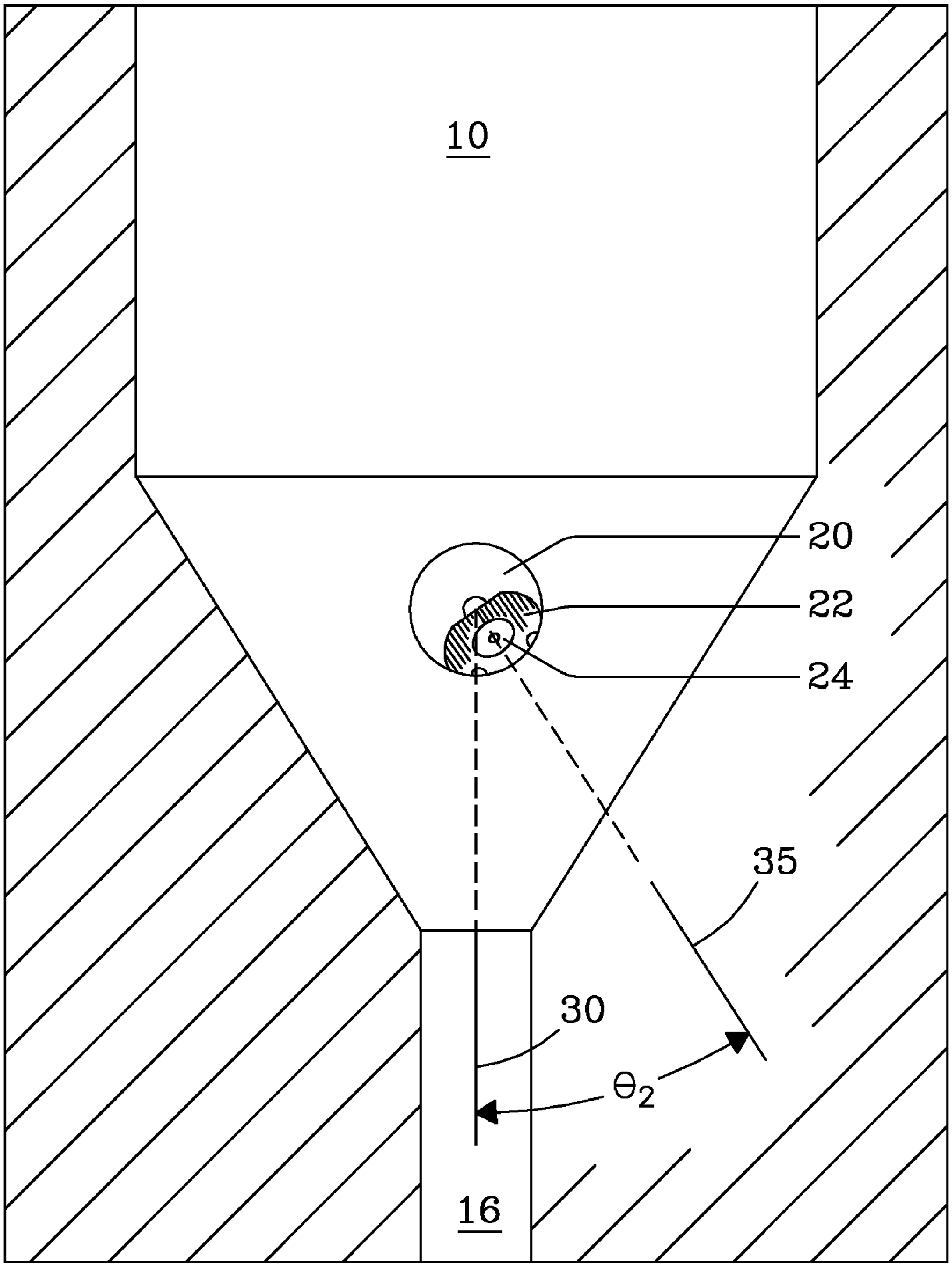
FIG. 2*d* presents a front vertical view of the article separation apparatus that shows the orientation of the article portal and its orientation angle.

FIG. **2*d* is a front vertical view of article separation apparatus 100 that shows an exemplary orientation of article portal 24. Portal 24 is preferably oriented at an (orientation) angle ($\theta_2$) of from plus or minus 40 degrees to 70 degrees relative to an axis 30 defined along the direction of levitating articles in containing means 10 and an axis 35 defined through the center of portal 24, but is not limited thereto. The portal is oriented by rotating conduit 20 clockwise or counterclockwise about its rotation axis until the desired angle is obtained. The angle ($\theta_1$) of the introduction surface 22 (FIG. 2*c*) and the orientation angle ($\theta_2$) of the portal prevent clogging of the portal that allow single articles to enter conduit 20**.

As indicated herein, apparatus 100 may be coupled to one or more unit operations or modules, described further herein with reference to FIG. **3*b***.

Figure 3A:
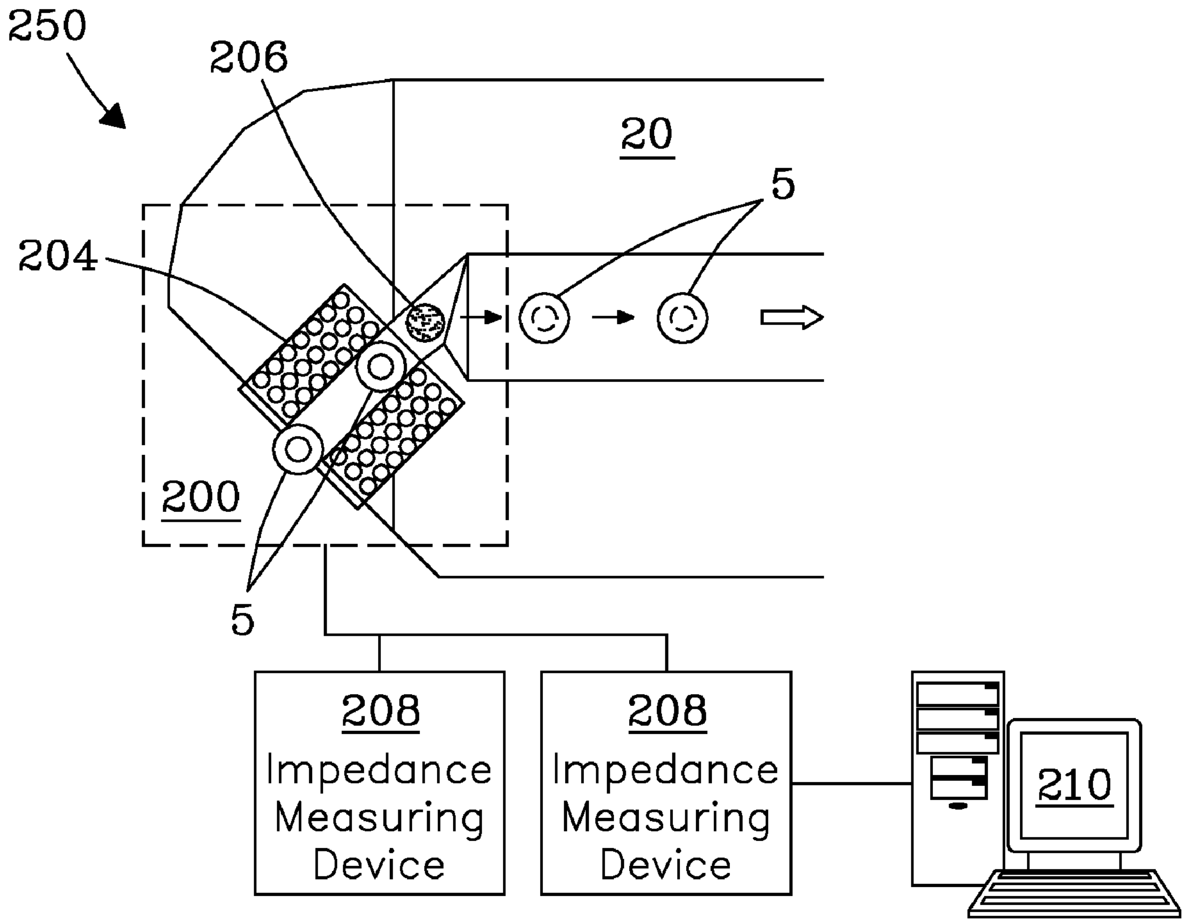
FIG. 3*a* presents a cross-sectional view of a system that includes an inspection module that couples with the article separation apparatus of the invention for inspection of, e.g., TRISO fuel particles, including layers thereof, according to an embodiment of the invention.

FIG. 3 presents a cross-sectional view of a system 250 for inspecting particles 5, e.g., TRISO fuel particles, including layers thereof, according to an embodiment of the invention. System 250 includes a module 200 (e.g., an inspection module) coupled with/to conduit 20 for inspection of particles 5. Inspection module 200 includes first sensor means 204 and second sensor means 206 for measuring physical properties of particles 5, respectively, including layers thereof, e.g., conductive and non-conductive properties. In the instant embodiment, first sensor means 204 is an inductive sensor 204 fabricated in-house for measuring impedance of particles 5 having various layer thicknesses and layer electrical conductivities in a changing magnetic field.

Sensor 204 includes an induction coil fabricated in-house consisting of 82 turns of 48-gauge (0.127 mm) copper wire, the coil having an interior diameter of approximately 0.98 mm and an outer diameter of approximately 1.2 mm. Dimensions are not limited thereto. In the instant embodiment, (inductive) surface of the coil of sensor 204 is positioned coincident with, or protruding from, the introduction surface and portal (described previously with reference to FIG. 1) thereby minimizing dead volume for articles introduced through sensor 204, but is not limited thereto. For example, coils of sensor 204 can be further positioned at displacement angles in the range from about 0 degrees to about 90 degrees with respect to a virtual axis projected through the center of the coils of sensor 204. Alternatively, the vertical plane of the coils of sensor 204 may be positioned at any angle in the range from about 0 degrees to about 90 degrees relative to the vertical plane of the portal (described previously with reference to FIG. 1). No limitations are intended.

Second sensor means 206 is a capacitance sensor 206 of a parallel (dual) plate design, each plate fabricated in-house from 20-gauge copper wire, with a non-conductive (e.g., polymer) coating applied to insulate the surface from particles 5 traversing between the sensing surfaces. Spacing between the parallel plates of second sensor means 206 depends on size of particles 5 being tested. In the instant embodiment, plate separation is selected in the range from about 0.350 mm to about 0.98 mm, but is not limited thereto. First 204 and second 206 sensor means of the instant embodiment are positioned such that particles 5 traverse coils of inductive sensor 204 at the center thereof and between the plates of capacitance (capacitive) sensor 206 positioned parallel to the flow of particles 5, but is not limited thereto. As will be understood by those of skill in the art, positioning of first 204 and second 206 sensor means within conduit 20 is not limited.

Distance between the sensing surface of sensor 204 or capacitance sensor 206 and particles 5 introduced to conduit 20 for inspection is minimized providing maximum "fill factor" for reliable impedance measurements. Fill factor is a key characteristic in evaluating sensor performance for assessing quality of an article, and is maximized by minimizing the distance between the inspecting surface of a sensor and an article being inspected for the greatest possible signal gain and/or resolution. Factors affecting the "fill factor" parameter include wire diameter, spacing, and distance to particles 5 being measured. First sensor means 204 and second sensor means 206 of inspection module 200 are co-located within conduit 20 whereby articles 5 entering conduit 20 are individually inspected. The physical geometry permits only one particle through sensor 204 or past sensor 206 at a given time providing for measurement of individual material properties by individual sensors. Currently, 300 particles 5 per minute can be measured, but is not limited thereto. Once inspected, particles 5 can be collected from conduit 20 as will be understood by those of skill in the art. No limitations are intended.

Figure 3B:
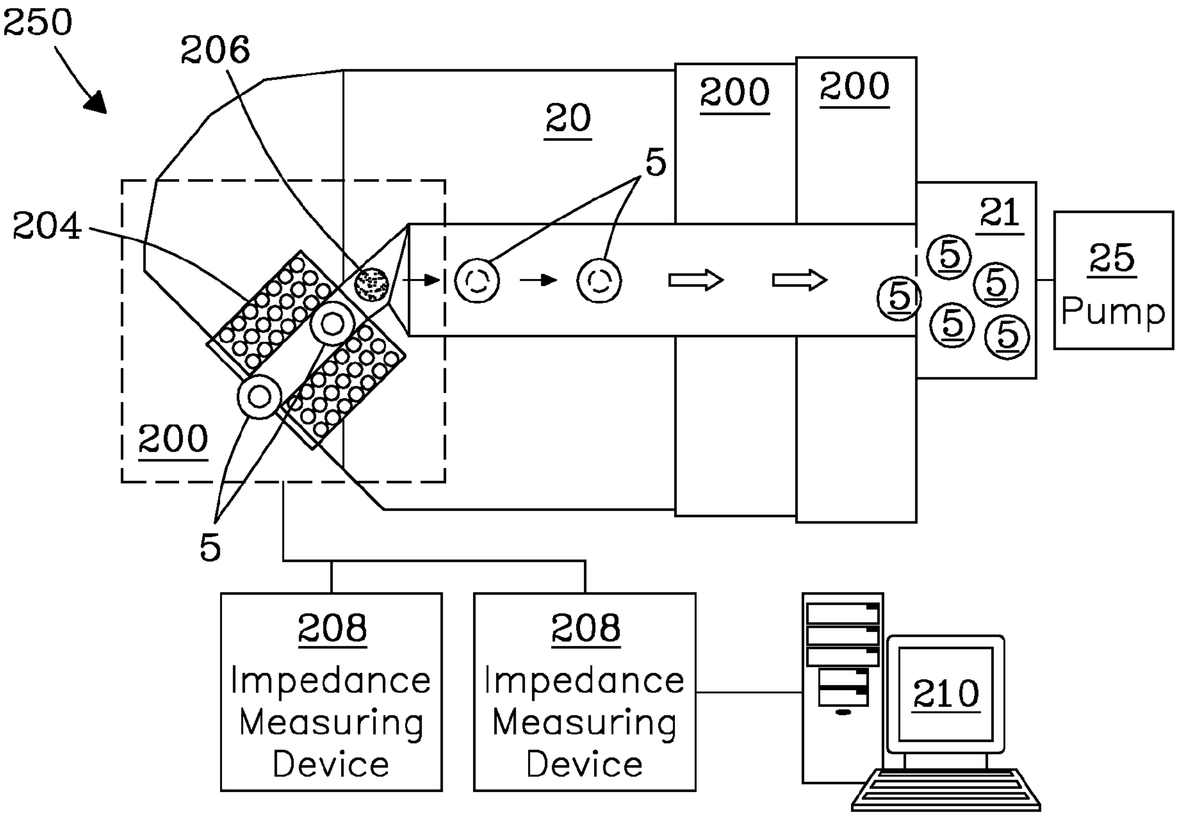
FIG. 3*b* presents a cross-sectional view of a system that includes one or more operation modules that couple with the article separation apparatus of the invention, according to another embodiment of the invention.

System 250 can be configured with one or more conduits 20 as described herein in reference to FIG. 1 and can also be coupled to one or more preselected modules, e.g., as described further herein in reference to FIG. 3*b*. All unit operation configurations as will be contemplated by those of skill in the art are encompassed herewith. No limitations are intended.

Control of apparatus 100, module 200 including components thereof, and data acquisition therefrom involves electronics, systems, and/or devices as will be implemented by those of skill in the art. In one embodiment, for example, measurement data from first sensor means 204 and second sensor means 206 are read using one or more measuring devices (e.g., an impedance measuring device) 208. Module 200 and measuring devices 208 can be further interfaced to a computer 210 (e.g., a PC) or programmable device controller (s) or like devices and/or systems for control and/or operation of the same as well as collection, storage, and/or manipulation of measurement data. In another illustrative example, positioning of, e.g., the inductive coil of sensor 204 may be remotely effected and controlled using a motor (e.g., servos or like devices) coupled to computer 210.

In addition, timing of sensor measurements may include optical sensing and triggering or manipulation (e.g., increasing) of the sampling frequency to allow collection of measurements for articles 5 centered in the selected sensors, e.g., sensors 204 or 206.

FIG. 3*b* presents a cross-sectional view of another embodiment of system 250 that includes three operation modules 200. In the figure, a first module 200, e.g., an inspection module described previously in reference to FIG. 3*a*, is positioned at the leading end of conduit 20 for inspection of articles 5 entering the conduit. In the figure, two additional modules 200 are shown coupled at the trailing end of conduit 20 that provide additional analyses or inspections, or that modify articles that proceed through the conduit within system 250. Modules include, but are not limited to, e.g., inspection modules that inspect various parts or materials of the articles, coating modules that provide coats of preselected material to the articles, quality assessment modules that assess various aspects of the articles including layers thereof, and various combinations of selected modules. Number and type of modules that can be coupled to the conduit are not intended to be limited. As will be further understood by those of skill in the art, the invention may be used in conjunction with additional components, vessels, and/or devices. For example, systems and/or devices for pumping, transferring, delivering, mixing, pressurizing, heating, and/or storing fluids, gases, and/or reagents, may be used. In addition the invention may be used in conjunction with other devices for automated collection and handling of articles. Further, the invention can be coupled to many and varied systems and processes employed in the manufacture of articles, e.g., material deposition whereby layers or coatings are applied. Thus, all processes and/or systems for handling and/or preparing articles are within the scope of the invention. No limitations are intended.

The invention can detect various defects. Defects include, but are not limited to, e.g., non-uniform layers, irregular shaped particles, thin layers, missing layers, thickness variations, size variations, and other microstructure variations among defective particles, including, e.g., radial cracking, disbanding between layers, density discrepancies. No limitations are intended. For example, defects most important to detect and characterize for fuel particles include, but are not limited to, e.g., missing buffer coating, heavy metal contamination, defective SiC, spatial defects penetrating the SiC layer, grain size and structure, free silicon or free carbon, structural flaws, impurities, thickness, anisotropy.

The description is further not intended to be limiting to types of particles, sizes, and/or parameters that can be inspected and/or measured. For example, inspection of particles in the micro- or nano-range can be done with appropriate air flows and equipment or device scaling. Further, physical parameters and/or properties can be measured for larger articles, including, but not limited to, e.g., tablets, pellets, and/or pharmaceuticals including various layers thereof.

Figure 4:
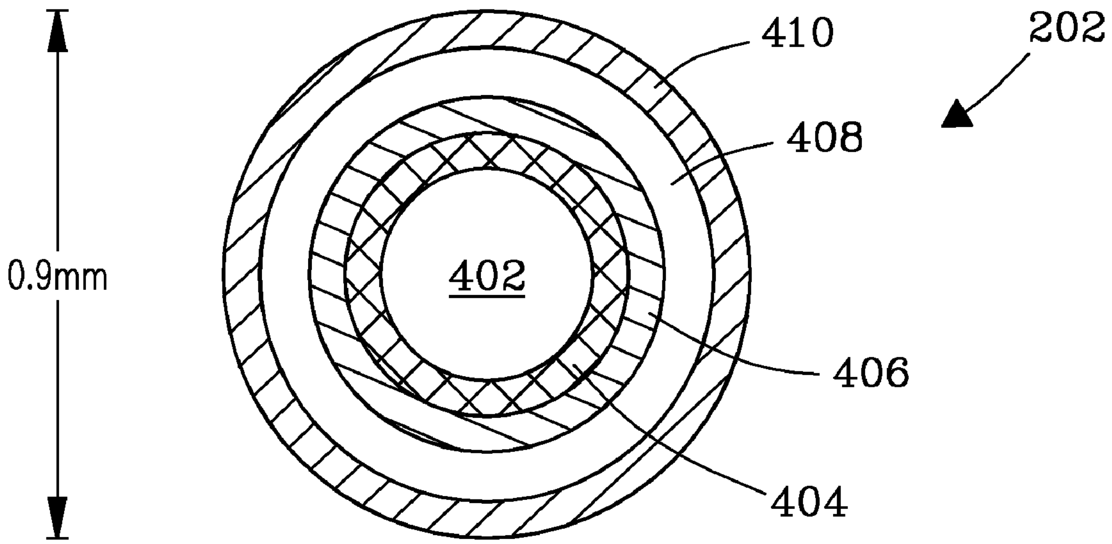
FIG. 4 is a cross-sectional view showing layers of a typical TRISO fuel particle tested in conjunction with the invention.

FIG. 4 is a cross-sectional view showing layers of a typical TRISO fuel particle 5 tested in conjunction with the invention. Layers include a kernel 402 composed of, e.g., depleted uranium dioxide ($DUO_2$), natural uranium oxycarbide (NUCO), uranium dioxide ($UO_2$), or zirconium dioxide ($ZrO_2$); a buffer layer of porous carbon 404; an inner layer of pyrolytic carbon (IPyC) 406; a layer of Silicon Carbide (SiC) 408; and an outer layer of pyrolytic carbon (OPyC) 410. TRISO and surrogate TRISO particles have diameters typically in the range from about 0.3 mm to about 1.0 mm, but are not limited thereto. Surrogate TRISO particles include a kernel 402 of $ZrO_2$ or other metal oxide.

Physical Properties and Quality Assessment

Table 1 lists material properties and layer thickness data for TRISO particles 5 with a surrogate kernel (e.g., $ZrO_2$) 402 described herein.

TABLE 1

Representative Material Properties of Surrogate TRISO Particles.

| | Density ρ(gm/cc) | Lame constant λ(GPa) | Lame constant μ(GPa) | Thickness/ Diameter (μm) |
|---|---|---|---|---|
| $ZrO_2$ kernel | 5.7 | 128.19 | 76.35 | 500 |
| Porous carbon buffer layer | 0.97 | 2 | 3.34 | 65 |
| IPyC layer | 1.875 | 5.5 | 10.5 | 35 |
| SiC layer | 3.19 | 77 | 199 | 35 |
| OPyC Layer | 1.825 | 5.5 | 10.5 | 40 |

For TRISO particles 5 tested, particle flaws and/or properties known to degrade fuel performance can be compiled. Properties and data for particles deemed to result in optimal fuel performance can also be compiled. Standard statistical analyses may then be used to compile and refine properties (e.g., for kernel diameter, coating layer thickness and spatial uniformity) suited for use in assessing quality or performance of individual articles in batches of, e.g., 30 to 40 articles or more. Results constitute a defect library of characterized particles that can be used to calibrate any nondestructive measurement method for automatic detection of particles having properties outside a specified range. No limitations are intended.

A difficulty in obtaining relevant information from modeling is the large number of unknown electrical properties of various layers of an article, e.g., electrical conductivity. These difficulties can be overcome by investigating particles having a single layer of a material of interest, e.g., a kernel 402 covered with, e.g., buffer 404, PyC (406 and/or 410) or SiC 408. In this approach, instead of working with the fully coated TRISO, only kernel 402 with a single layer is investigated. This approach makes it possible to solve equations having the same number of unknown parameters as the number of measurable parameters. Further, this approach reduces the number of parameters being investigated simultaneously, for each measurement technique, at any one time. Once the NDE measurement sensitivity to the properties of a single-layer is understood then the combined effects from each layer in the full TRISO are easier to deconvolute. A second approach is to use reasonable approximations for any unknown parameters and then use several different characterized particle measurements to adjust the quality assessment model to fit the measurements. The next step is to establish signatures for each flaw type of interest expected to affect particle fuel performance.

The following examples detail the testing of these various modalities and are intended to promote a further understanding of the present invention. Example 1 describes results obtained from inductive response methods to particle defects, as measured by deviations from a specified benchmark or "ideal" particle. Example 2 details results obtained using system 250 configured with inspection module 200 that includes a capacitive sensor 206 for measuring physical properties of a TRISO fuel particle 5. Example 3 details results obtained using system 250 configured with inspection module 200 including an inductive sensor 204 and a capacitive sensor 206 for measuring physical properties of surrogate TRISO fuel particles 202, as described herein.

EXAMPLE 1

Inspection Results from Testing of TRISO Fuel Particles (Inductive Impedance Data)

Example 1 describes results obtained from inspection of TRISO fuel particles using an inductive sensor.

Figure 6:
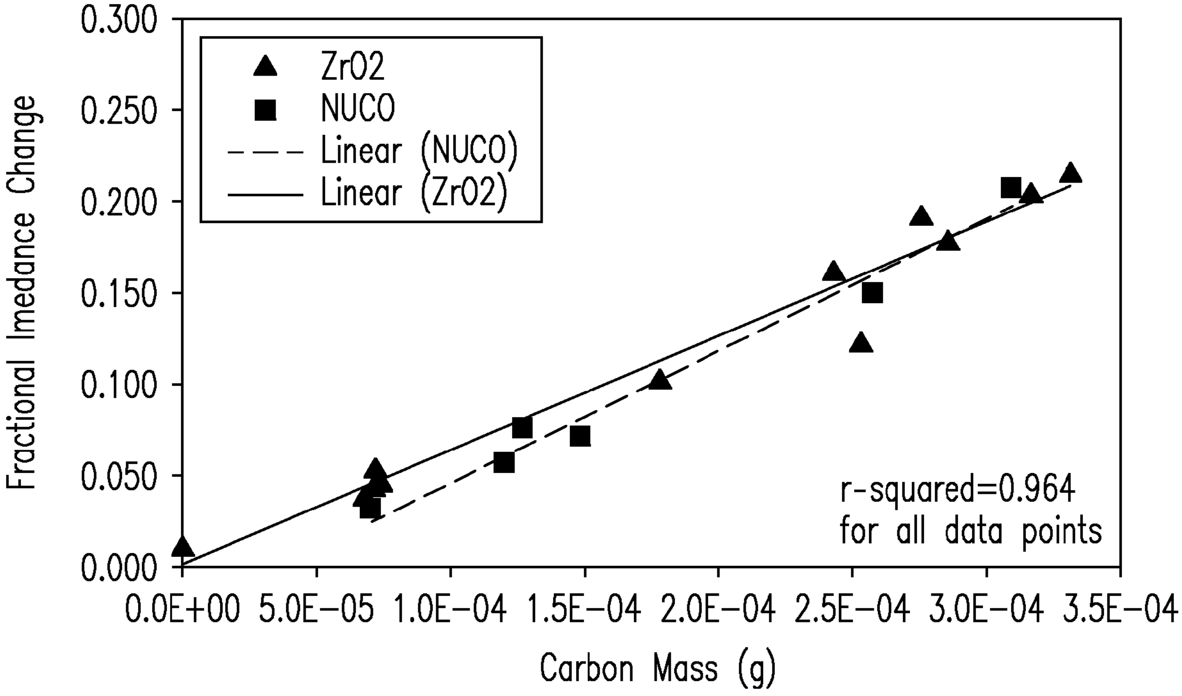
FIG. 6 is a graph of fractional inductive impedance data collected for TRISO fuel particles using an inductive sensor plotted as a function of carbon mass.
Figure 7A:
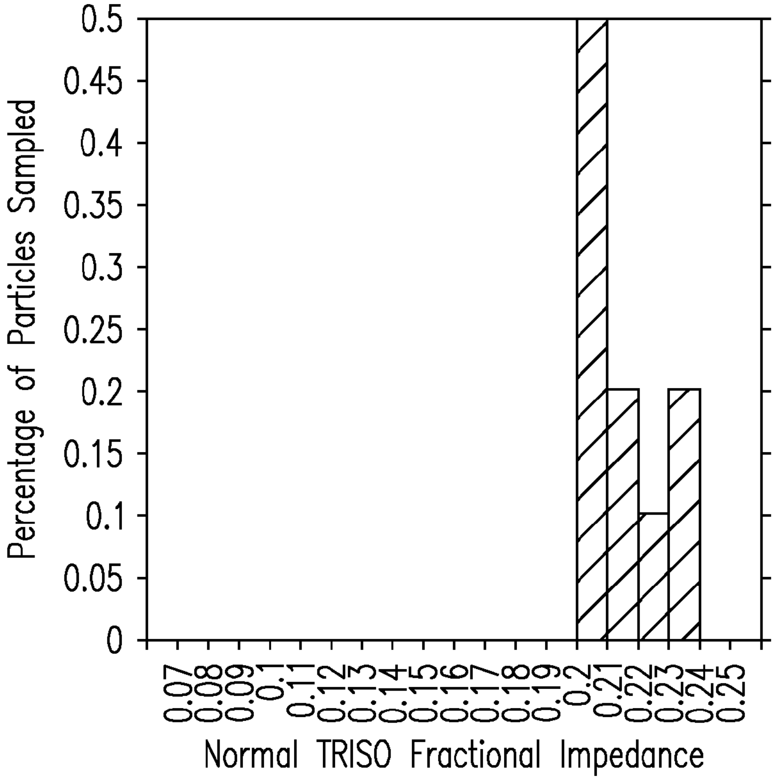
FIGS. 7*a*-7*b* compare fractional impedance values measured for TRISO particles having a normal buffer layer thickness and particles having a thin or improper buffer layer thickness, respectively.
Figure 7B:
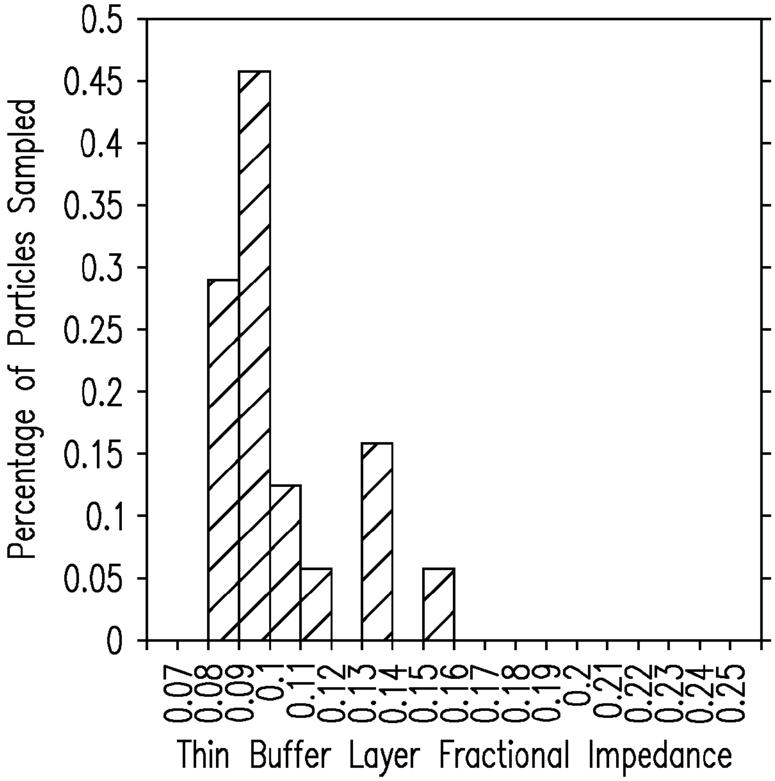

Experimental. Fully coated (normal) TRISO fuel particles 5 [both (NUCO kernel) and surrogate ($ZrO_2$ kernel)] were inspected using system 250 as described herein configured with inspection module 200 that included an inductive sensor 204. Normalized fractional inductive impedance data are presented in FIG. 5 and FIG. 6 as a function of pyrolytic carbon volume (cc) and carbon mass (g), respectively. Impedance values were also measured for normal TRISO particles 5 with a buffer layer of a typical thickness (101.2 μm) and for TRISO particles 5 having a thin or improper buffer layer thickness (18.5 μm). FIG. 7*a* and FIG. 7*b* compare fractional impedance values measured for the normal and defective particles 5, respectively.

Figure 5:
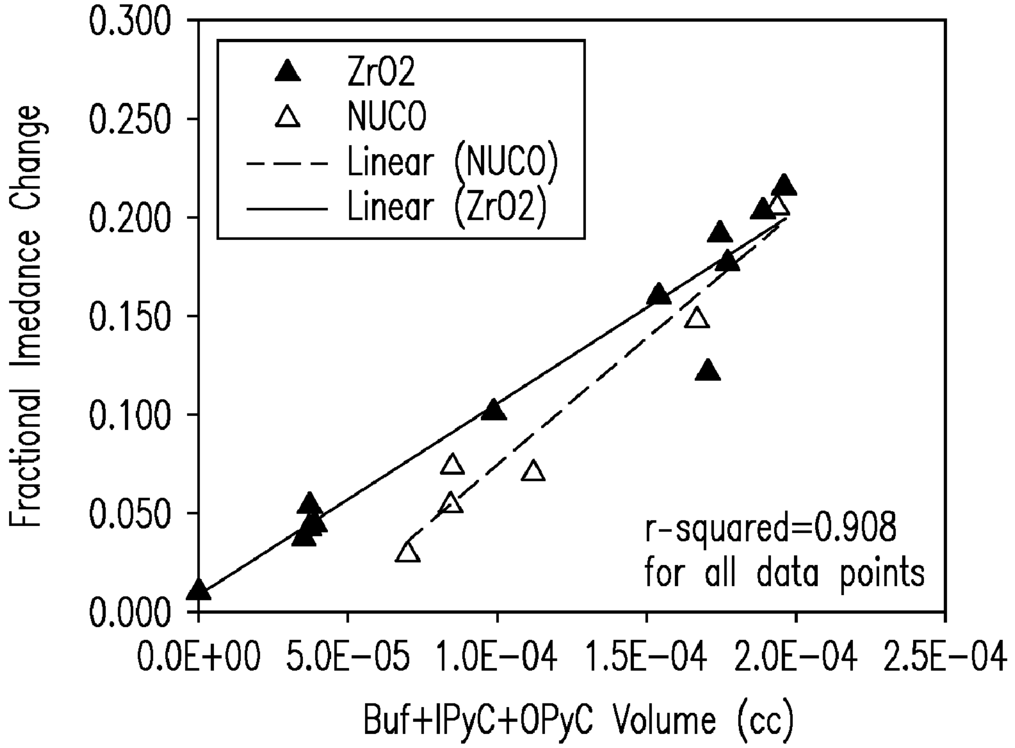
FIG. 5 is a graph of fractional inductive impedance data collected for TRISO fuel particles using an inductive sensor plotted as a function of particle volume (buffer+inner pyrolytic (IPyC)+outer pyrolytic (OPyC)).

Results. In FIG. 5 and FIG. 6, fractional inductive impedance change is plotted against total pyrolytic carbon volume [e.g., volume of porous carbon buffer layer (buffer)+volume of inner pyrolytic carbon layer (IPyC)+volume of outer pyrolytic carbon layer (OPyC)] and carbon mass, respectively. The correlation coefficient for fractional inductive impedance change vs. pyrocarbon volume is 0.908 and the correlation coefficient for fractional inductive impedance change vs. pyrocarbon mass is 0.964. Data show a high degree of correlation to both pyrocarbon volume as well as mass. Data are further distinguished by particle type (e.g., NUCO vs. Surrogate).

FIGS. 7*a* and 7*b* compare fractional impedance values for normal TRISO particles 5 with a normal buffer thickness (101.2 μm) and TRISO particles 5 having a thin or improper buffer layer thickness (18.5 μm), respectively. In FIG. 7*a*, fractional impedance values for normal particles 5 tested were in the range from about 0.2 to about 0.4. In FIG. 7*b*, particles 5 with the defective buffer exhibited impedance values in the range from about 0.08 to about 0.16, with a majority of particles 5 having impedance values more particularly in the range from about 0.08 to about 0.12. Differences in impedance values for the two classes of particles 5 are clearly sufficient to distinguish between normal and defective particles 5 for quality-control or assessment purposes.

EXAMPLE 2

Inspection Results from Testing of TRISO Fuel Particles (Capacitive Impedance Data)

Example 2 details results obtained using system 250 configured With inspection module 200 that includes a capacitive sensor 206 for measuring physical properties of a TRISO fuel particle 5.

Figure 8:
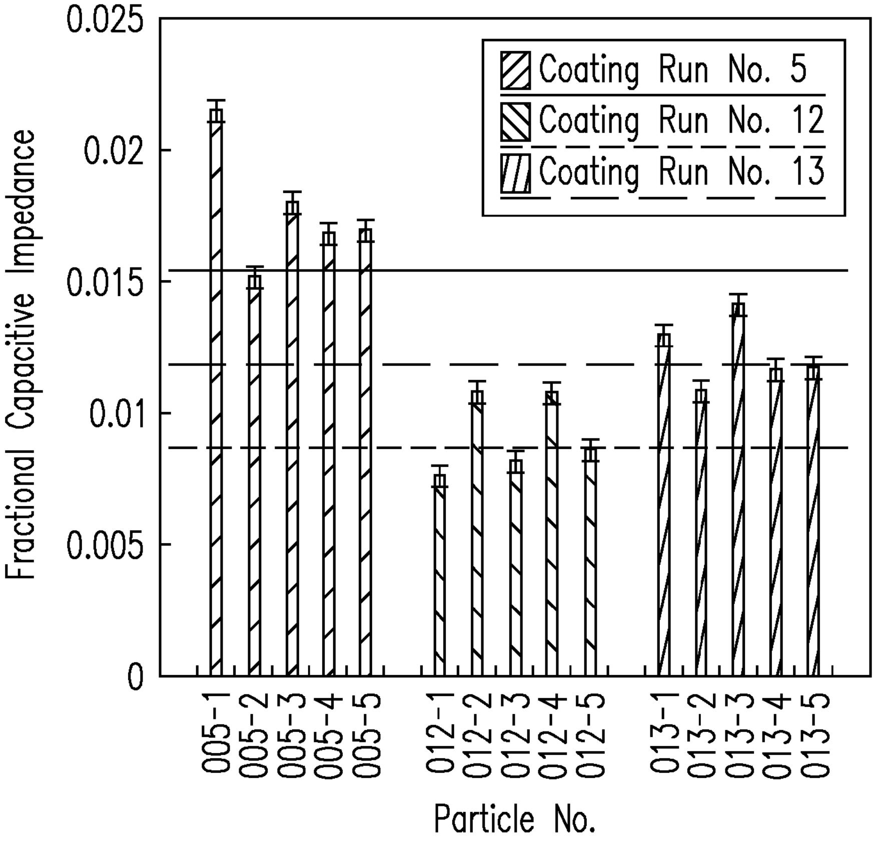
FIG. 8 is a graph of capacitive impedance data measured for three sets of randomly selected TRISO particles.
Figure 9:
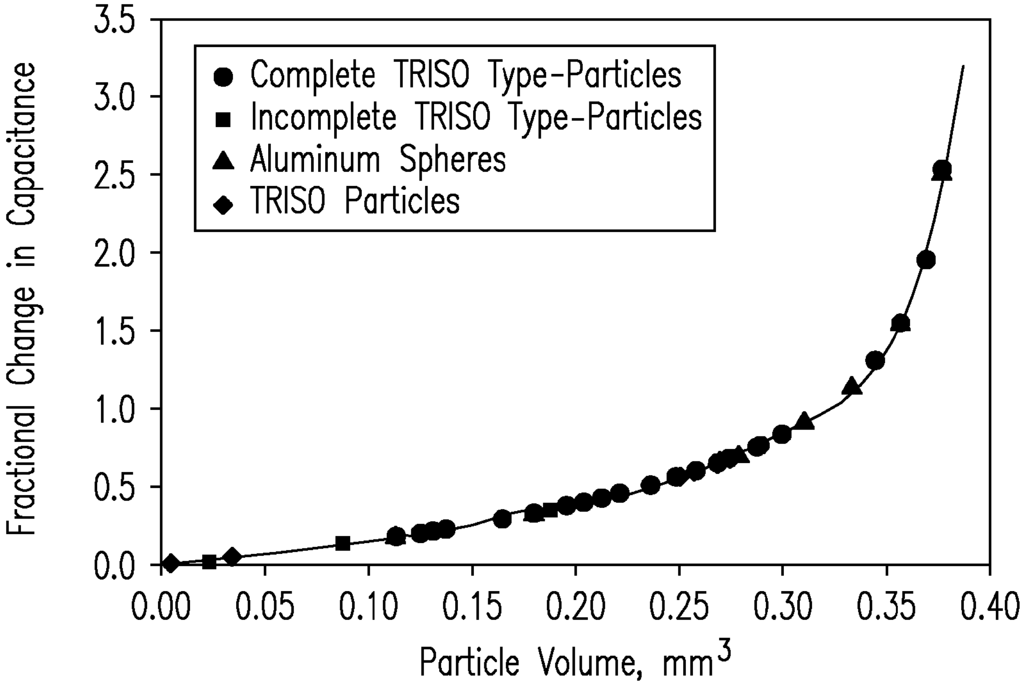
FIG. 9 is a graph showing data for fractional change in capacitance for TRISO fuel particles plotted as a function of total carbon volume (buffer+IPyC+OPyC). Data for reference aluminum spheres of approximately equal volume are also shown.

Experimental. TRISO fuel particles 5 from three different coating Runs were inspected using system 250 configured with inspection module 200 that included a capacitive sensor 206. Set 1 consisted of fully coated TRISO particles 5. Set 2 consisted of particles 5 with a missing SiC layer. Set 3 consisted of particles 5 with a thin SiC layer. By measuring voltage and current flow across the plates it was possible to determine change in capacitance and capacitive impedance due to presence of TRISO particles 5 passed between plates of sensor 206. FIG. 8 plots fractional capacitive impedance results for particles 5 from the three different coating runs. FIG. 9 plots fractional capacitive change for TRISO fuel particles 5 and for aluminum spheres plotted as a function of volume.

Results. FIG. 8 is a plot showing of capacitive impedance for TRISO particles 5 measured from the three coater runs. In the figure, data from each coater run are clearly distinguished. For example, fully coated TRISO particles 5 (set 1) have higher impedance values compared to those with no SiC layer (set 2) and thin SiC layer (set 3). While variations in kernel size can cause significant capacitive impedance variations for a given coating run, results obtained herein indicate it is possible to detect differences in layer thickness, as evidenced for the SiC layer thickness. Such differences can be exploited to distinguish between various particles 5 inspected. In particular, results show potential for detecting and differentiating normal, thin layer, and/or missing layer TRISO fuel particles 5 at speeds necessary for 100 percent inspection of particles in various batches or production runs.

FIG. 9 is a graph showing fractional change in capacitance for TRISO fuel particles 5 plotted as a function of total carbon volume (buffer+IPyC+OPyC); data for reference aluminum spheres of approximately equal volume are also shown. Fractional change in capacitance, ($C_f$), is given by equation 1:

$$C_f=(C-C_0)/C_0 \quad [1]$$

where C and $C_0$ are, respectively, the capacitance with and without particle 5 present. The curve in FIG. 9 represents a fill-factor function describing the increase in capacitance as the air gap between plates (electrodes) of capacitive sensor 206 are filled by a conductive material of increasing volume. If the outer layer of a particle 5 is even slightly conductive (even the assumed conductivity of SiC, 100 S/m, is sufficient), charges distribute themselves on its surface to form an equipotential surface. Additional charges are required on the electrode surfaces to support the increased voltage gradient in the spaces between particle 5 and electrodes. This increases capacitance, as given by equation [2]:

$$C=Q/V \quad [2]$$

where Q is the charge and V is the fixed voltage between the electrodes. For particles 5 passing between parallel plates of capacitive sensor 206, capacitance (C) is given by equation [3]:

$$C=\kappa*\epsilon_0*A/d \quad [3]$$

where $\kappa$ is the dielectric constant of a material between the plate (e.g., air, articles, or etc.), $\epsilon_0$ is the permittivity of free space, A is the surface area of each electrode, and d is the distance between the electrodes.

Results show measured fractional capacitance change values correlate well with the total volume of particles 5. In FIG. 9, this is demonstrated by the fact that values measured for aluminum spheres lie on the same curve as values measured for fully coated and improperly coated TRISO particles 5 having nearly identical volumes. Capacitive sensor 206 is suitable for detecting differences in, or inspecting, articles 5 with different volumes.

EXAMPLE 3

Inspection Results from Testing of TRISO Fuel Particles (Combined Inductive & Capacitive Impedance Data)

Example 3 details results obtained using system 250 configured with an inspection module 200 including an inductive sensor 204 and a capacitive sensor 206 for measuring physical properties of surrogate TRISO fuel particles 5, as described herein.

Experimental. Fully coated TRISO fuel particles 5 were Inspected using both inductive sensor 204 and capacitive sensor 206 and impedance data collected. Data are plotted in FIGS. 10 and 11.

Figure 10:
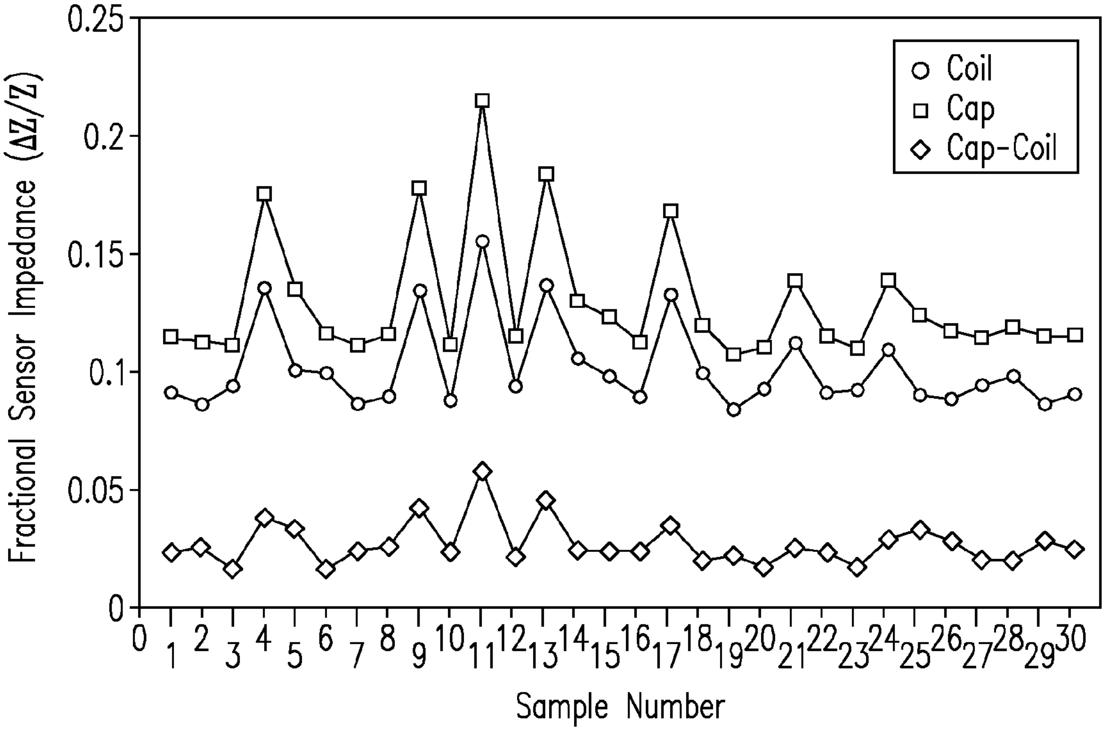
FIG. 10 is a graph of fractional impedance data from simultaneous measurement of TRISO fuel particles using an inductive sensor and a capacitive sensor plotted as a function of sample number.

Results. FIG. 10 is a plot of fractional impedance values for sensor 204 and 206 as a function of sample number. Also plotted are the differences between sensor fractional impedance values (ΔZ for inductive and capacitive values). Particles with a full coating but with a thin buffer were also examined using the dual sensor measurement method. FIG. 10 plots measurement results showing the fractional impedance and the fractional impedance difference between the capacitive and inductive sensors. Results show the inductive impedance is less than the capacitive impedance. Reduction in inductive impedance is attributed to less conductive material being present and interacting with the coil of sensor 204.

Figure 11:
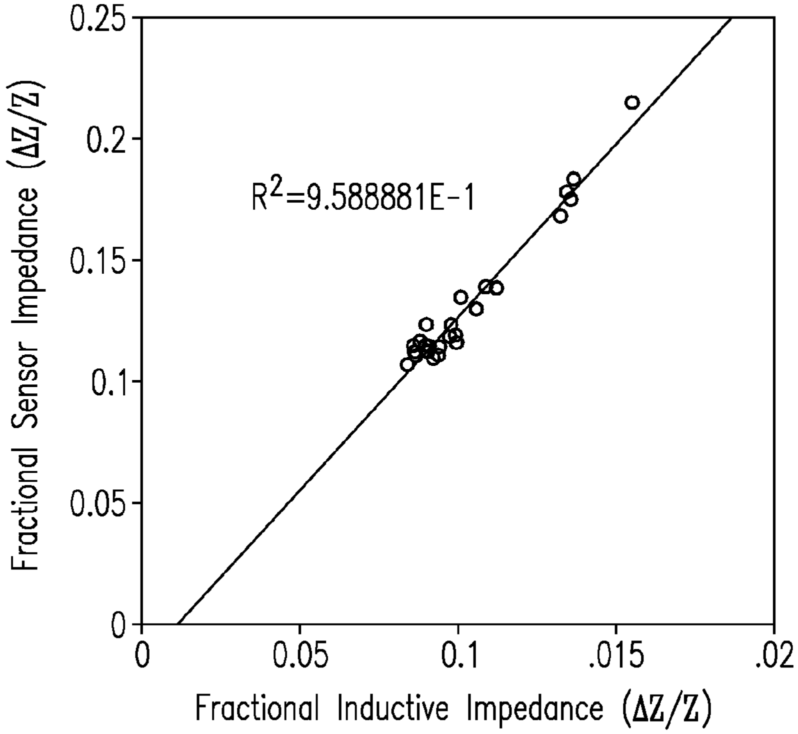
FIG. 11 is a graph of fractional inductive impedance values for sensor plotted as a function of fractional capacitive impedance values for sensor.

FIG. 11 is a plot of fractional inductive impedance values collected using sensor 204 plotted as a function of fractional capacitive impedance values for sensor 206. Results show a high degree of correlation ($R^2=0.959$) between the measured values, indicating that both sensors 204 and 206 are sensitive to effects caused by the same physical property. The kernel diameter is the most widely varying parameter for particles 5 tested. Kernel diameter can have a significant effect on volume of all layers applied in a coating run at a required thickness. Thickness variation in any single layer coating can also affect volume of all successive layers, but typically, individual layers do not vary in thickness as much as the kernel diameter.

While the preferred embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

We claim:

1. An apparatus for separating a single article from a group of articles, comprising:
   - a containing means for containing one or more articles that define a group of articles, said containing means comprises an inlet for introducing said one or more articles into said containing means and at least one outlet;
   - a levitating means for levitating said one or more articles in said group of articles within said containing means in a levitation direction; and
   - a conduit operatively coupled to said at least one outlet, said conduit includes an introduction surface and a portal, wherein the plane of said introduction surface is oriented at an angle ($\theta_1$) with respect to an axis defined along the length of said conduit of about 45 degrees; and
   - said portal is oriented at an angle of rotation ($\theta_2$) with respect to said levitation direction and a virtual axis projected through the center of said portal of from about 0 degrees to about 90 degrees;
   - whereby single articles are separated from said group of articles and transported away from said group of articles via a differential pressure.

2. The apparatus of claim 1, wherein said conduit is selected from the group consisting of induction tube, vacuum tube, pick-up tube, and combinations thereof.

3. The apparatus of claim 1, wherein said containing means is selected from the group consisting of: hoppers, feeders, funnels, enclosures, containers, magnetic bottles, chambers, and combinations thereof that houses said group of articles.

4. The apparatus of claim 1, wherein said levitation means is selected from the group consisting of: aerators, fluidizers, channeling devices, charging devices, anti-static charging devices, projecting devices, pneumatic devices, propeller devices, and combinations thereof that levitates said group of articles.

5. The apparatus of claim 1, wherein said introduction surface of said conduit is flat or round.

6. The apparatus of claim 1, wherein said conduit is rotatable clockwise or counterclockwise about said axis defined along the length of said conduit.

7. The apparatus of claim 1, further comprises one or more modules operatively coupled to said conduit selected from the group consisting of: inspection modules, coating modules, quality assessment modules, and combinations thereof that provides a preselected analysis of, or operation on, said, single article transported within said conduit.

8. The apparatus of claim 7, wherein said one or more modules includes an inspection module with a sensor selected from the group consisting of: inductive sensors, capacitive sensors, optical sensors, acoustic sensors, magnetic sensors, infra-red sensors, X-ray sensors, tomographic sensors, radiographic sensors, coating sensors, and combinations thereof.

9. The apparatus of claim 8, wherein said inspection module includes a sensor that is an inductive sensor that includes an inductive coil.

10. The apparatus of claim 9, wherein said inductive coil of said sensor is operatively coupled with said portal and is coincident with, or protrudes from, said introduction surface of said conduit to minimize dead volumes for said single article introduced to said conduit.

11. The, apparatus of claim 9, wherein said inductive coil of said sensor has a position that includes a preselected angle with respect to said axis defined through the center of said portal in the range from about 0 degrees to about 90 degrees.

12. The apparatus of claim 8, wherein said one or more modules includes an inductive sensor that provides a measurement of a conductive property of said single article.

13. The apparatus of claim 8, wherein said one or more modules includes an inspection module that comprises a capacitive sensor that provides a measurement of a non-conductive property of said single article.

14. The apparatus of claim 8, wherein said one or more modules includes an inspection module that provides a measurement of a physical property of said single article or a layer thereof.

15. The apparatus of claim 14, wherein said physical property measurement of said single article is selected from the group consisting of: size, presence of a material, absence of a material, thickness, shape, conductance, non-conductance, dielectric constant, variances in same, and combinations thereof.

16. The apparatus of claim 14, wherein said physical property measurement of said single article is a physical property measurement of a layer selected from the group consisting of: thickness, anisotropy, uniformity, presence of a material, absence of a material, non-conductance, conductance, dielectric constant, variances in same, and combinations thereof.

17. The apparatus of claim 14, wherein said physical property measurement of said single article is a measurement of a conductive property.

18. The apparatus of claim 14, wherein said physical property measurement of said single article is a measurement of a non-conductive property.

19. The apparatus of claim 14, wherein said physical property measurement of said single article includes a measurement of a defect selected from the group consisting of: layer variations, concentricity variations, uniformity variations, spatial uniformity variations, cracks, flats, and combinations thereof.

20. The apparatus of claim 8, wherein said one or more modules includes at least one inspection module.

21. The apparatus of claim 8, wherein said one or more modules includes a coating module or a coating inspection module.

* * * * *